(12) United States Patent
Nichols

(10) Patent No.: US 6,491,233 B2
(45) Date of Patent: Dec. 10, 2002

(54) VAPOR DRIVEN AEROSOL GENERATOR AND METHOD OF USE THEREOF

(75) Inventor: Walter A. Nichols, Chesterfield, VA (US)

(73) Assignee: Chrysalis Technologies Incorporated, Richmond, VA (US)

(*) Notice: Subject to any disclaimer, the term of this patent is extended or adjusted under 35 U.S.C. 154(b) by 0 days.

(21) Appl. No.: 09/742,395

(22) Filed: Dec. 22, 2000

(65) Prior Publication Data

US 2002/0079377 A1 Jun. 27, 2002

(51) Int. Cl.[7] .............................. B05B 1/24; B05B 7/16; B05B 1/30
(52) U.S. Cl. ........................ 239/128; 239/134; 239/135; 239/569
(58) Field of Search ................................ 239/128, 135, 239/337, 13, 10, 132, 133, 134, 136, 139, 569

(56) References Cited

U.S. PATENT DOCUMENTS 2,896,856 A  7/1959  Kravits (List continued on next page.)

FOREIGN PATENT DOCUMENTS

| BE | 354004 A | 9/1928 |
|---|---|---|
| BE | 354094 A | 9/1928 |
| DE | 1036470 B1 | 8/1958 |
| EP | 0358114 A | 3/1990 |
| EP | 0642802 A2 | 5/1996 |
| FR | 667979 A | 10/1929 |
| HU | 168128 B | 11/1977 |
| HU | 216121 B | 3/1991 |
| HU | 207457 A | 4/1993 |
| HU | P953409 | 6/1994 |
| WO | 94/09842 A | 5/1994 |
| WO | 98/17131 | 4/1998 |

OTHER PUBLICATIONS

Notification of Transmittal of the International Search Report or the Declaration dated Apr. 24, 2002 for PCT/US01/44810.

Barry, P.W. et al. "In Vitro Comparison of the Amount of Salbutamol Available for Inhalation From Different Formulations Used with Different Spacer Devices" Eur Respir J 1997; 10:1345–1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

(List continued on next page.)

Primary Examiner—Lesley D. Morris
Assistant Examiner—Davis Hwu
(74) Attorney, Agent, or Firm—Burns, Doane, Swecker & Mathis, LLP

(57) ABSTRACT

An aerosol generator includes a fluid supply which supplies fluid to a fluid passage, a main heater which heats the fluid into a gaseous state and a preheater which delivers a volume of fluid to the main heater. The preheater can be located in or adjacent a metering chamber which receives a predetermined volume of fluid, the preheater heating a portion of the fluid so as to form a vapor bubble which ejects the remaining fluid from the chamber. An outlet of the aerosol generator is arranged to receive the volatilized fluid formed by the main heater and direct the volatilized fluid out of the fluid passage. The aerosol generator can be used to generate aerosols containing medicated materials.

21 Claims, 1 Drawing Sheet

U.S. PATENT DOCUMENTS

| | | | |
|---|---|---|---|
| 3,084,698 | A | 4/1963 | Smith |
| 3,157,179 | A | 11/1964 | Paullus et al. |
| 3,162,324 | A | 12/1964 | Houser |
| 3,431,393 | A | 3/1969 | Katsuda |
| 3,486,663 | A | 12/1969 | Humphrey |
| 3,658,059 | A | 4/1972 | Steil |
| 3,716,416 | A | 2/1973 | Adlhart et al. |
| 3,750,961 | A | 8/1973 | Franz |
| 3,847,304 | A | 11/1974 | Cohen |
| 3,859,398 | A | 1/1975 | Havstad |
| 3,902,635 | A | 9/1975 | Jinotti |
| 3,903,883 | A | 9/1975 | Pecina et al. |
| 3,904,083 | A | 9/1975 | Little |
| 3,967,001 | A | 6/1976 | Almaula et al. |
| 3,987,941 | A | 10/1976 | Blessing |
| 3,993,246 | A | 11/1976 | Erb et al. |
| 3,995,371 | A | 12/1976 | O'Keefe |
| 4,042,153 | A | 8/1977 | Callahan et al. |
| 4,060,082 | A | 11/1977 | Lindberg et al. |
| 4,077,542 | A | 3/1978 | Petterson |
| 4,161,282 | A | 7/1979 | Erb et al. |
| 4,162,501 | A | 7/1979 | Mitchell et al. |
| 4,215,708 | A | 8/1980 | Bron |
| 4,231,492 | A | 11/1980 | Rios |
| 4,258,073 | A | 3/1981 | Payne |
| 4,259,409 | A | 3/1981 | Arnold |
| 4,261,356 | A | 4/1981 | Turner et al. |
| 4,289,003 | A | 9/1981 | Yang |
| 4,291,838 | A | 9/1981 | Williams |
| 4,303,083 | A | 12/1981 | Burruss, Jr. |
| 4,383,171 | A | 5/1983 | Sinha et al. |
| 4,391,308 | A | 7/1983 | Steiner |
| 4,395,303 | A | 7/1983 | Weir |
| 4,433,797 | A | 2/1984 | Galia |
| 4,471,892 | A | 9/1984 | Coleman |
| 4,512,341 | A | 4/1985 | Lester |
| 4,575,609 | A | 3/1986 | Fassel et al. |
| 4,627,432 | A | 12/1986 | Newell et al. |
| 4,649,911 | A | 3/1987 | Knight et al. |
| 4,682,010 | A | 7/1987 | Drapeau et al. |
| 4,695,625 | A | 9/1987 | Macdonald |
| 4,700,657 | A | 10/1987 | Butland |
| 4,730,111 | A | 3/1988 | Vestal et al. |
| 4,735,217 | A | 4/1988 | Gerth et al. |
| 4,744,932 | A | 5/1988 | Browne |
| 4,749,778 | A | 6/1988 | Fukuzawa et al. |
| 4,762,995 | A | 8/1988 | Browner et al. |
| 4,776,515 | A | 10/1988 | Michalchik |
| 4,790,305 | A | 12/1988 | Zoltan et al. |
| 4,811,731 | A | 3/1989 | Newell et al. |
| 4,819,625 | A | 4/1989 | Howe |
| 4,819,834 | A | 4/1989 | Thiel |
| 4,829,996 | A | 5/1989 | Noakes et al. |
| 4,837,260 | A | 6/1989 | Sato et al. |
| 4,848,374 | A | 7/1989 | Chard et al. |
| 4,871,115 | A | 10/1989 | Hessey |
| 4,871,623 | A | 10/1989 | Hoopman et al. |
| 4,877,989 | A | 10/1989 | Drews et al. |
| 4,911,157 | A | 3/1990 | Miller |
| 4,922,901 | A | 5/1990 | Brooks et al. |
| 4,926,852 | A | 5/1990 | Zoltan et al. |
| 4,935,624 | A | 6/1990 | Henion et al. |
| 4,941,483 | A | 7/1990 | Ridings et al. |
| 4,947,875 | A | 8/1990 | Brooks et al. |
| 4,974,754 | A | 12/1990 | Wirz |
| 4,982,097 | A | 1/1991 | Slivon et al. |
| 4,992,206 | A | 2/1991 | Waldron |
| 5,021,802 | A | 6/1991 | Allred |
| 5,044,565 | A | 9/1991 | Alexander |
| 5,056,511 | A | 10/1991 | Ronge |
| 5,060,671 | A | 10/1991 | Counts et al. |
| 5,063,921 | A | 11/1991 | Howe |
| 5,096,092 | A | 3/1992 | Devine |
| 5,125,441 | A | 6/1992 | Mette |
| 5,133,343 | A | 7/1992 | Johnson, IV et al. |
| 5,134,993 | A | 8/1992 | van der Linden et al. |
| 5,135,009 | A | 8/1992 | Müller et al. |
| 5,144,962 | A | 9/1992 | Counts et al. |
| 5,151,827 | A | 9/1992 | Ven et al. |
| 5,178,305 | A | 1/1993 | Keller |
| 5,184,776 | A | 2/1993 | Minier |
| 5,217,004 | A | 6/1993 | Blasnik et al. |
| 5,226,441 | A | 7/1993 | Dunmire et al. |
| 5,228,444 | A | 7/1993 | Burch |
| 5,230,445 | A | 7/1993 | Rusnak |
| 5,231,983 | A * | 8/1993 | Matson et al. ......... 128/207.14 |
| 5,259,370 | A | 11/1993 | Howe |
| 5,290,540 | A | 3/1994 | Prince et al. |
| 5,298,744 | A | 3/1994 | Mimura et al. |
| 5,299,565 | A | 4/1994 | Brown |
| 5,322,057 | A * | 6/1994 | Raabe et al. ............ 128/203.12 |
| 5,327,915 | A | 7/1994 | Porenski et al. |
| 5,342,180 | A | 8/1994 | Daoud |
| 5,342,645 | A | 8/1994 | Eisele et al. |
| 5,349,946 | A | 9/1994 | McComb |
| 5,395,445 | A | 3/1995 | Bohanan |
| 5,421,489 | A | 6/1995 | Holzner, Sr. et al. |
| 5,462,597 | A | 10/1995 | Jubran |
| 5,474,059 | A | 12/1995 | Cooper |
| 5,509,557 | A | 4/1996 | Jimarez et al. |
| 5,515,842 | A | 5/1996 | Ramseyer et al. |
| 5,522,385 | A * | 6/1996 | Lloyd et al. ............ 128/203.26 |
| 5,556,964 | A | 9/1996 | Hofstraat et al. |
| 5,564,442 | A | 10/1996 | MacDonald et al. |
| 5,565,677 | A | 10/1996 | Wexler |
| 5,575,929 | A | 11/1996 | Yu et al. |
| 5,585,045 | A | 12/1996 | Heinonen et al. |
| 5,617,844 | A | 4/1997 | King |
| 5,642,728 | A | 7/1997 | Andersson et al. |
| 5,674,860 | A | 10/1997 | Carling et al. |
| 5,682,874 | A | 11/1997 | Grabenkort et al. |
| 5,730,158 | A | 3/1998 | Collins et al. |
| 5,743,251 | A * | 4/1998 | Howell et al. .......... 128/200.14 |
| 5,756,995 | A | 5/1998 | Maswadeh et al. |
| 5,765,724 | A | 6/1998 | Amberg et al. |
| 5,823,178 | A | 10/1998 | Lloyd et al. |
| 5,839,430 | A | 11/1998 | Cama |
| 5,855,202 | A | 1/1999 | Andrade |
| 5,856,671 | A | 1/1999 | Henion et al. |
| 5,863,652 | A | 1/1999 | Matsumura et al. |
| 5,869,133 | A | 2/1999 | Anthony et al. |
| 5,872,010 | A | 2/1999 | Karger et al. |
| 5,878,752 | A | 3/1999 | Adams et al. |
| 5,881,714 | A | 3/1999 | Yokoi et al. |
| 5,894,841 | A | 4/1999 | Voges |
| 5,906,202 | A | 5/1999 | Schuster et al. |
| 5,914,122 | A | 6/1999 | Otterbeck et al. |
| 5,932,249 | A | 8/1999 | Gruber et al. |
| 5,932,315 | A | 8/1999 | Lum et al. |
| 5,934,272 | A | 8/1999 | Lloyd et al. |
| 5,934,273 | A | 8/1999 | Andersson et al. |
| 5,944,025 | A | 8/1999 | Cook et al. |
| 5,954,979 | A | 9/1999 | Counts et al. |
| 5,957,124 | A | 9/1999 | Lloyd et al. |
| 5,970,973 | A | 10/1999 | Gonda et al. |
| 5,970,974 | A | 10/1999 | Van Der Linden et al. |
| 5,978,548 | A | 11/1999 | Holmstrand et al. |
| 5,993,633 | A | 11/1999 | Smith et al. |
| 6,014,970 | A | 1/2000 | Ivri et al. |
| 6,053,176 | A | 4/2000 | Adams et al. |
| 6,054,032 | A | 4/2000 | Haddad et al. |

| | | |
|---|---|---|
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,071,554 A | 6/2000 | Isomura et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 6/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,151,827 A * | 11/2000 | Smith et al. ............ 43/129 |
| 6,155,268 A | 12/2000 | Takeuchi |
| 6,158,431 A | 12/2000 | Poole |
| 6,158,676 A * | 12/2000 | Hughes ............ 239/405 |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 * | 8/2001 | Hunt ............ 123/549 |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 2001/0032647 A1 | 10/2001 | Schuster et al. |

OTHER PUBLICATIONS

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron; P.R. & Farr, S.J.) Interpharm Press, Buffalo Grove, IL 1998 pp. 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

Copending Application No. 09/742,322 naming Kenneth A. Cox, Walter Allen Nichols, F. Murphy Sprinkel, Jr., Douglas D. Mcrae and William R. Sweeney as inventor(s) and filed on Dec. 22, 2000.

Notification of Transmittal of International Preliminary Examination Report for PCT/US01/44810 dated Sep. 10, 2002.

* cited by examiner

VAPOR DRIVEN AEROSOL GENERATOR AND METHOD OF USE THEREOF

BACKGROUND OF THE INVENTION

1. Field of the Invention

The present invention relates generally to aerosol generators and, more particularly, to vapor driven aerosol generators. The aerosol generators of the invention are able to generate aerosols without requiring the use of compressed gas propellants. The present invention also relates to methods for generating an aerosol. The present invention has particular applicability to the generation of aerosols containing medicated material.

2. Description of the Related Art

Aerosols are gaseous suspensions of fine solid or liquid particles and are useful in a wide variety of applications. For example, medicated liquids and powders may be administered in aerosol form. Such medicated aerosols include, for example, materials which are useful in the treatment of respiratory ailments, in which case the aerosols may be inhaled into a patient's lungs. Aerosols may also be used in non-medicinal applications including, for example, dispensing air fresheners and insecticides and delivering paints and/or lubricants.

In aerosol inhalation applications, it is typically desirable to provide an aerosol having an average mass median particle diameter of less than 2 microns to facilitate deep lung penetration. Most known aerosol generators are incapable of generating aerosols having an average mass median particle diameter less than 2 microns. Also, in certain applications, it is generally desirable to deliver medicated material at high flow rates, for example, above 1 mg per second. Most known aerosol generators suited for delivering medicated material are incapable of delivering material at such high flow rates while maintaining a suitable average mass median particle diameter. In addition, most known aerosol generators deliver an imprecise amount of aerosol compared with the amount of aerosol that is intended to be delivered.

The related art discloses aerosol generators which employ various techniques for delivering an aerosol. A particularly useful technique involves volatilizing a fluid and ejecting the volatilized fluid into the atmosphere. The volatilized fluid subsequently condenses, thereby forming an aerosol. See, for example, commonly assigned U.S. Pat. No. 5,743,251, the entire contents of which document are hereby incorporated by reference. Such aerosol generators may eliminate or conspicuously reduce some or all of the aforementioned problems associated with the known aerosol generators. However, since these aerosol generators employ heat-generating systems, heat resistive material and, in some cases, various control devices, pumps and valves, the manufacture and assembly of such aerosol generators can be complicated and expensive.

In light of the foregoing, there exists a need in the art for the provision of an aerosol generator which overcomes or conspicuously ameliorates the above described shortcomings in the related art. Accordingly, it is an object of the present invention to provide a vapor driven aerosol generator which produces an aerosol from a fluid by volatilizing the fluid and directing the volatilized fluid therefrom.

Other objects and aspects of the present invention will become apparent to one of ordinary skill in the art upon review of the specification, drawings and claims appended hereto.

SUMMARY OF THE INVENTION

The invention provides an aerosol generator which includes a fluid passage having an upstream and a downstream end, a heater arranged to heat fluid in the passage into a gaseous state, a fluid supply arranged to provide a fluid to the upstream end of the passage, a preheater located between the fluid supply and the main heater, the preheater including a heating element which heats a portion of the fluid in the passage into a gaseous state such that fluid in the passage downstream of the heating element is driven through the passage in a downstream direction.

The heating element is preferably located in a chamber having a predetermined volume and/or the fluid supply includes a valve which closes the passage when the heating element heats the fluid into a gaseous state. If desired, the heating element can be located along an inner wall of a metering chamber, the metering chamber being sized to receive a predetermined volume of fluid to be emitted as an aerosol from the aerosol generator. The passage can be located in an organic or inorganic material selected from one or more polymer, metal and ceramic materials. For instance, the passage can be located in a ceramic laminate wherein the passage is defined by a recess in a surface of a first ceramic layer and a surface of a second ceramic layer bonded to the first ceramic layer. The heating element can comprise a layer of resistance heating material located along one or more walls of the passage.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 1:
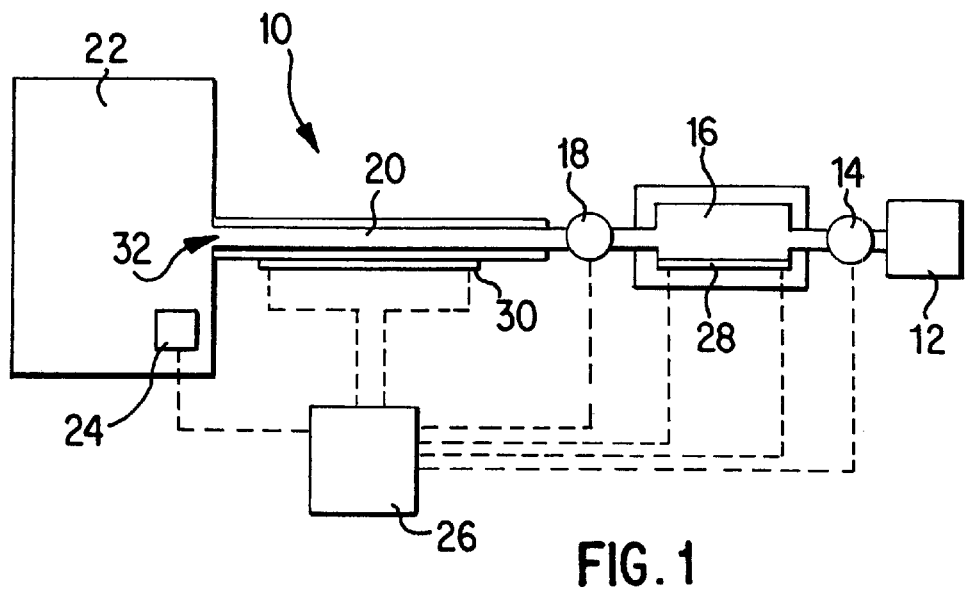
FIG. 1 is a schematic diagram of an exemplary aerosol generator in accordance with the invention.

When referring to the drawing figures, like reference numerals designate identical or corresponding elements throughout the several figures.

FIG. 1 shows a vapor driven aerosol generator 10 in accordance with one embodiment of the invention. As shown, the aerosol generator 10 includes a source 12 of fluid, a valve 14, a chamber 16, a valve 18, a passage 20, a mouthpiece 22, an optional sensor 24 and a controller 26. In addition, the aerosol generator 10 includes a preheater 28 and a main heater 30. The controller 26 includes suitable electrical connections and ancillary equipment such as a battery which cooperates with the controller for operating the valves 14, 18, the sensor 24 and the heaters 28, 30. In operation, the valve 14 can be opened to allow a desired volume of fluid from the source 12 to enter the chamber 16 during which time the valve 18 can be closed to prevent the incoming fluid from advancing into the passage 20. Filling of the chamber 16 can occur prior to or subsequent to detection by the sensor 24 of vacuum pressure applied to the mouthpiece 22 by a user attempting to inhale aerosol from the inhaler 10. Once the chamber 16 contains a predetermined volume of fluid, the controller 26 closes valve 14 and opens valve 18 while operating the preheater 28 to drive the fluid into the passage 20. While the fluid passes through the passage 20, the controller 26 operates the main heater 30 to heat the fluid to a suitable temperature for volatilizing the fluid therein. The volatilized fluid exits an outlet 32 of the passage 20 and the volatilized fluid forms an aerosol which can be inhaled by a user drawing upon the mouthpiece 22.

The aerosol generator shown in FIG. 1 can be modified to utilize different fluid supply arrangements. For instance, the fluid source can comprise a delivery valve which delivers a predetermined volume of fluid to the chamber 16 in which case the chamber 16 need not be sized to hold a precise volume of liquid. Alternatively, the chamber can be sized to hold a predetermined volume of fluid and the fluid supply can comprise a pressurized source of fluid which fills the chamber when valve 14 is opened. The preheater 28 heats the fluid in the chamber 16 such that a vapor bubble is formed which expands and drives the remaining liquid from the chamber 16 into the passage 20. If desired, valves 14, 18 could be omitted and the fluid source 12 can include a delivery arrangement which supplies a predetermined volume of fluid to the chamber 16. Further, the main heater 30 can be an individual heater or a plurality of heaters arranged to volatilize the liquid in passage 20. In the case of manual operations, the sensor 24 can be omitted such as in the case where the aerosol generator 10 is operated manually by a mechanical switch, electrical switch or other suitable technique.

Figure 2:
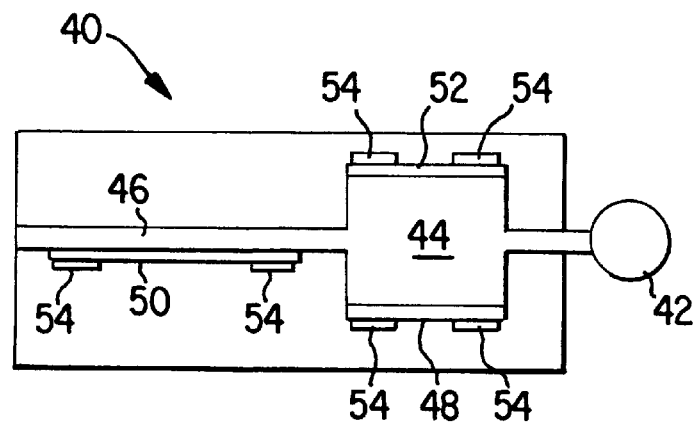
FIG. 2 is a cross section of an exemplary aerosol generator in accordance with the invention.

FIG. 2 shows a top cutaway view of a vapor driven aerosol generator 40 in accordance with another embodiment of the invention. As shown, the aerosol generator 40 includes a fluid supply 42, a chamber 44, a passage 46, a preheater 48 and a main heater 50. The preheater 48 can be arranged on one side of the chamber 44 such that fluid in the chamber 44 is heated to form a vapor bubble which expands and drives the remaining fluid in the chamber 44 into the passage 46. If desired, an additional preheater 52 can be provided in the chamber 44 in order to provide additional heating of the fluid. The heaters 48, 52 extend horizontally along bottom and top walls of the chamber 44. The heaters 48, 50, 52 are preferably thin films of resistance heating material. In order to pass electrical current through the heaters, the heaters can be in electrical contact with suitable electrical contacts 54. A suitable power source such as a battery can be used to deliver sufficient direct current to the contacts 54 in order to heat the heaters 48, 50, 52 to desired temperatures. Further, operation of the heaters and supply of fluid from the fluid source 42 can be controlled by a suitable controller as in the case of the first embodiment.

Like the embodiment shown in FIG. 1, the embodiment shown in FIG. 2 can be modified to incorporate different fluid supply arrangements and/or heating arrangements. However, it is preferred that the chamber 44 include at least one preheater therein or associated therewith such that fluid in the chamber 44 can be heated to form a vapor bubble which drives the fluid in the chamber 44 into the passage 46.

Figure 3:
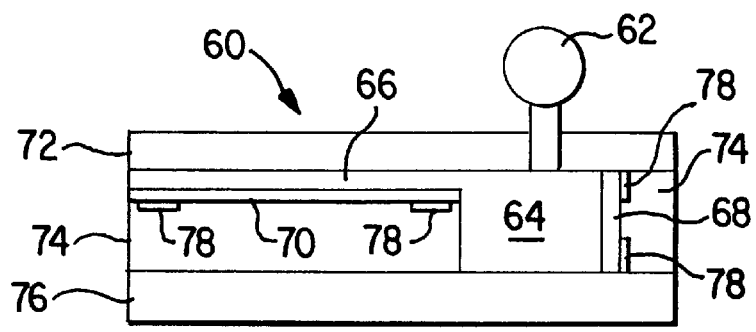
FIG. 3 is a cross section of another exemplary aerosol generator in accordance with the invention.

FIG. 3 shows a side view of a third embodiment of a vapor driven aerosol generator in accordance with the invention. As shown, the aerosol generator 60 includes a fluid supply 62, a chamber 64, a passage 66, a preheater 68 and a main heater 70. The aerosol generator 60 can be formed from solid state components such as layers 72, 74, 76 of metal, organic or ceramic material such as a polymer material or ceramic material. If desired, layers 74 and 76 can comprise a single layer which has been machined or etched to form the passage 66 and the chamber 64. Alternatively, one or more layers can be interposed between the layers 74 and 76 so as to form the passage 66 and the chamber 64. As in the case of the embodiment shown in FIG. 2, the heaters 68, 70 can be supplied power by contacts 78. The heater 68 is arranged to extend vertically along an inner sidewall of the chamber 64. In arrangements wherein the heater contacts the fluid, it is desirable to coat the heater with a material which is nonreactive with the fluid, e.g., glass or metal such as stainless steel.

The fluid may include any material capable of volatilization by the aerosol generator. In a preferred embodiment, the fluid does not decompose when exposed to the heat required for volatilization thereof. The fluid preferably includes a medicated material such as, for example, a material that is useful in the treatment of respiratory ailments. In such applications, the generated aerosol may be inhaled into a user's lungs. Alternatively, the fluid may include a non-medicated material.

In the foregoing embodiments, the fluid passage can be defined by a capillary tube or a channel in a multi-layered arrangement wherein the layers are formed from a heat-resistant material that is preferably capable of withstanding the temperatures and pressures generated in the fluid passage. The heat-resistant material is more preferably capable of withstanding repeated heating cycles. Also, the heat-resistant material preferably does not react with the fluid contained in the fluid passage. The heat-resistant material may include, for example, alumina, zirconia, silica, aluminum silicate, titania, yttria-stabilized zirconia or mixtures thereof, preferably alumina. The layers may be of any size suitable for aerosol generation. According to a preferred embodiment, each layer can have a length of from about 1 to 100 mm, more preferably about 15 mm; a width of from about 1 to 100 mm, more preferably about 15 mm; and a thickness of from about 0.001 to 10 mm, more preferably about 0.076 mm.

The layers can be configured to at least partially define the fluid passage. In an exemplary embodiment of the present invention, a channel is in a layer or the channel can be defined by adding one or more layers of material between first and second layers. The layers can be attached together, thereby enclosing the channel therebetween. In this manner, the channel defines the fluid passage.

The layers may be attached together using various techniques, including, for example, adhesive bonding. The adhesive material used to attach the layers is preferably capable of withstanding repeated heating cycles and may include, for example, a metal, a cement, an epoxy, an acrylic, a cyanoacrylic or mixtures thereof, preferably an acrylic cement. Alternatively, other techniques may be used to attach the layers together such as, for example, mechanical or metallurgical bonding such as a brazing material.

The fluid passage is preferably linear to facilitate the flow of the fluid therethrough. Alternatively, the fluid passage can be non-linear in two or three dimensions such as in the case where the direction of fluid flow through the passage contains at least one turn. An outlet at the downstream end of the fluid passage can be sized to achieve a desired aerosol particle size distribution. In a preferred embodiment, the outlet is circular and has a diameter of about from 0.01 to 5 mm, more preferably about 0.1 mm.

The outlet may be disposed at an angle, for example, 10 to 160°, with respect to the axis of fluid flow within the fluid passage, to direct the flow of the volatilized fluid out of the fluid passage in a desired direction. According to an alternative embodiment, the fluid passage can extend through a side wall of the layers, and the outlet can be defined by the furthest downstream portion of the fluid passage. A conduit (not shown) may be connected to receive the volatilized fluid from the outlet to further direct the flow of volatilized fluid in a desired direction. Such a conduit can have a diameter of from about 0.01 to 5 mm.

In a preferred embodiment, a valve and/or a pump can be used to control the flow of fluid from the fluid supply to the fluid passage. The valve and/or the pump may be manually operated or a controller may manipulate the valve and/or the pump based on various parameters including, for example, the amount of time the valve remains in the open position, or the volumetric amount of fluid that is supplied to the fluid passage. In this manner, the valve and/or the pump may enable the liquid supply to deliver a predetermined volume of fluid in liquid phase to the fluid passage. In an alternative embodiment, the fluid in liquid phase can be contained in a chamber, and the fluid can be delivered by compressing the fluid in the chamber using a piston.

The fluid supply provides the fluid to be volatilized in fluid phase to the fluid passage. The fluid in liquid phase may be stored in the liquid supply at a pressure above atmospheric to facilitate delivery of the fluid to the fluid passage. In an exemplary embodiment, the fluid supply comprises a refillable storage chamber formed of a material suitable for containing the fluid to be volatilized. Alternatively, the fluid supply comprises a disposable storage chamber which, upon exhaustion of the fluid, is discarded and replaced by a new storage chamber.

The fluid passage may contain any amount of fluid in liquid phase which is capable of being volatilized by the heater of the aerosol generator. For example, the fluid passage may have a liquid volumetric capacity of from about $1 \times 10^{-6}$ ml to 0.005 ml. Alternatively, the fluid passage may have a liquid volumetric capacity of greater than about 0.005 ml, preferably from about 0.1 ml to 1.0 In aerosol inhalation applications, the fluid passage may have a liquid volumetric capacity which is sufficient for containing a predetermined amount of fluid that comprises a metered quantity of fluid.

The main heater for heating the fluid passage and the preheater for heating the chamber preferably include a film forming an electrically resistive heating material which is different from the heat-resistant material used to form the layers of the aerosol generator. For example, the resistive material may include a pure metal, metal alloy or metal compound such as platinum, titanium nitride, stainless steel, nickel chromium or mixtures thereof. Additional resistive materials include composite layers such as self-regulating heater materials. The main heater may be sized to be capable of generating a sufficient amount of heat to vaporize the fluid present in the fluid passage. In a preferred embodiment, the main heater has a length of from about 1 to 100 mm, more preferably about 10 mm; a width of from about 0.1 to 10 mm, more preferably about 0.5 mm; a thickness of from about 1 to 10 microns, more preferably about 3 microns; and an electrical resistance of from about 0.1 to 10 ohms, more preferably about 0.65 ohm.

Using a material for forming the heaters which is different from the material used to form the layers allows the resistance through the heaters to be easily adjusted by varying various parameters including, for example, the dimensions and amount of heat produced by the heaters may be adjusted for various applications. the material of the heaters. In this manner, the resistance of the heaters and the The resistive material of the heaters may be attached to the layers using various techniques. For example, the resistive material may be sputtered, printed, bonded or coated upon the layers. Deposition by sputtering includes, for example, DC magnetron sputter deposition. Deposition by bonding includes, for example, eutectically bonding the resistive material using sputtered material including, for example, copper or copper sheet material. Alternatively, vacuum evaporation, chemical deposition, electroplating and chemical vapor deposition may be used to deposit the resistive material.

Various factors contribute to the stability of the bond between the heater and the layers. For example, to enhance bonding, the arithmetic average of the surface roughness of the surface upon which the resistive material is disposed preferably is greater than or equal to about 1 microinch, more preferably from about 1 to 100 microinches, and most preferably from about 12 to 22 microinches. In addition, the heat-resistant material of the layers and the resistive material of the heater preferably have comparable coefficients of thermal expansion to minimize or prevent thermally induced delamination.

In a preferred embodiment, the heater is in electrical contact with first and second contacts which pass an electrical current through the heater. In this embodiment, the power supply which provides the electrical current to the heater is in electrical contact with the first and second contacts.

The first and second contacts of the heater are preferably formed from a material which has a lower resistance than that of the resistive material of the heater. For example, the first and second contacts typically include copper or a copper alloy such as, for example, phosphor bronze and Si bronze, and preferably copper or a copper alloy comprising at least 80% copper. Use of such materials prevents or reduces the heating of the contacts prior to the heating of the heater. The contacts are sized to be capable of passing an electrical current through the heater. The contacts may be attached to the layers and/or heater using any of the techniques used to attach the resistive material to the layers, as discussed above.

In each of the above embodiments, a single heater or multiple heaters may be used for the main heater or preheater. The use of multiple heaters for the main heater in the aerosol generator may enable a more uniform distribution of heat within the fluid passage. Alternatively, the use of multiple heaters may enable different zones of the fluid passage to be maintained at different temperatures. Such differing temperature zones in the fluid passage may be useful in fluid temperature control devices, as discussed in U.S. application Ser No. 09/742,322, filed Dec. 22, 2000, the entire contents of which document are incorporated by reference herein.

The aerosol generator may generate an aerosol either on an intermittent or continuous basis. For intermittent generation of an aerosol, for example, the liquid supply provides the fluid in liquid phase to the fluid passage each time the generation of an aerosol is desired. The valve and/or the pump may be used to actuate the flow of fluid from the liquid supply to the fluid passage. The remaining fluid in liquid phase between the liquid supply and the fluid passage is prevented from traveling back into the liquid supply by any suitable device such as the valve and/or the pump to prevent expansion of the volatilized fluid in the direction opposite the outlet.

For generating an intermittent aerosol in inhalation applications, the aerosol generator is preferably provided with a puff-actuated sensor, which is preferably arranged inside a mouthpiece disposed proximate to the outlet. The puff-actuated sensor can be used to actuate the valve and/or the pump and the heaters so that the liquid supply provides the fluid in liquid phase to the chamber, the preheater drives the fluid into the fluid passage, and the fluid is volatilized by the main heater. The puff-actuated sensor is preferably sensitive to pressure drops occurring in the mouthpiece when a user draws on the mouthpiece. The aerosol generator is preferably provided with circuitry such that, when a user draws on the mouthpiece, the valve and/or pump supply fluid in liquid phase to the fluid passage and the heaters are heated by the power supply.

A puff-actuated sensor suitable for use in the aerosol generator includes, for example, Model 163PC01D35 silicon sensor, manufactured by the MicroSwitch division of Honeywell, Inc., located in Freeport, Ill., or SLP004D 0-4" $H_2O$ Basic Sensor Element, manufactured by SenSym, Inc., located in Milpitas, Calif. Other known flow-sensing devices, such as those using hot-wire anemometry principles, may also be suitable for use with the aerosol generator. While the invention has been described in detail with reference to preferred embodiments thereof, it will be apparent to one skilled in the art that various changes can be made, and equivalents employed, without departing from the scope of the invention.

What is claimed is:

1. An aerosol generator, comprising:
    a fluid passage having an upstream and a downstream end;
    a main heater arranged to heat liquid in the fluid passage into a gaseous state;
    a fluid supply arranged to provide a fluid to the upstream end of the fluid passage; and
    a preheater located between the fluid supply and the main heater, the preheater including a heating element which heats a portion of fluid into a gaseous state such that fluid in the fluid passage downstream of the heating element is driven through the fluid passage in a downstream direction.

2. The aerosol generator of claim 1, wherein the heating element is located in a chamber having a volume larger than the portion of the fluid heated into a gaseous state by the preheater.

3. The aerosol generator of claim 1, wherein the fluid supply includes a valve which closes the fluid passage when the heating element heats the portion of the fluid into a gaseous state.

4. The aerosol generator of claim 1, wherein the heating element is located along an inner wall of a metering chamber, the metering chamber being sized to receive a predetermined volume of fluid to be emitted as an aerosol from the aerosol generator.

5. The aerosol generator of claim 1, wherein the fluid passage is located in an organic or inorganic material selected from one or more polymer, metal and ceramic materials.

6. The aerosol generator of claim 1, wherein the fluid passage is located in a ceramic laminate, the fluid passage being defined by a recess in a surface of at least one ceramic layer.

7. The aerosol generator of claim 6, wherein the ceramic laminate includes layers of a material selected from the group consisting of alumina, zirconia, silica and mixtures thereof.

8. The aerosol generator of claim 1, wherein the heating element comprises a layer of resistance heating material located along one or more walls of the fluid passage.

9. The aerosol generator of claim 1, wherein the preheater is arranged to directly contact the fluid in the fluid passage.

10. The aerosol generator of claim 1, wherein the preheater is arranged to conduct heat through an intermediate layer of material to the fluid in the fluid passage.

11. The aerosol generator of claim 1, wherein the preheater comprises a material selected from the group consisting of platinum, titanium nitride, stainless steel, nickel chromium and mixtures thereof.

12. The aerosol generator of claim 1, wherein the preheater is sputtered, printed, adhesively bonded or coated on a layer of electrically insulating material.

13. The aerosol generator of claim 1, wherein the fluid passage extends in a linear or nonlinear direction.

14. The aerosol generator of claim 1, wherein the preheater is in electrical contact with first and second contacts which pass an electrical current through the preheater.

15. The aerosol generator of claim 1, wherein the fluid comprises a medicated material.

16. The aerosol generator of claim 1, further comprising a power supply for heating the preheater.

17. A method for generating an aerosol, comprising the steps of:
    (a) supplying fluid to a fluid passage wherein a first portion of the fluid passage is heated by a preheater and a second portion of the fluid passage is heated by a main heater which volatilizes the fluid;
    (b) heating the preheater so as to volatilize a portion of the fluid in the fluid passage so as to form a vapor bubble which conveys non-volatilized fluid to the second portion of the fluid passage;
    (c) heating the main heater so as to volatilize the fluid in the second portion of the fluid passage; and
    (d) forming an aerosol by ejecting the volatilized fluid out of an outlet of the fluid passage.

18. The method of claim 17, wherein the preheater heats the fluid in the fluid passage by thermal conduction.

19. The method of claim 17, wherein the preheater heats the fluid by thermal conduction through an intermediate layer of material.

20. The method of claim 17, wherein the fluid passage comprises a channel disposed in a multilayer arrangement and the volatilized fluid is ejected through an opening in a surface of the multilayer arrangement.

21. A method of making an aerosol generator, comprising:
    forming a fluid passage having an upstream and a downstream end;
    forming a main heater arranged to heat liquid in the fluid passage into a gaseous state;
    forming a fluid supply arranged to provide a fluid to the upstream end of the fluid passage; and
    forming a preheater located between the fluid supply and the main heater, the preheater including a heating element which heats a portion of fluid into a gaseous state such that fluid in the fluid passage downstream of the heating element is driven through the fluid passage in a downstream direction.

* * * * *

UNITED STATES PATENT AND TRADEMARK OFFICE
CERTIFICATE OF CORRECTION

PATENT NO. : 6,491,233 B2  
DATED : December 10, 2002  
INVENTOR(S) : Walter A. Nichols It is certified that error appears in the above-identified patent and that said Letters Patent is hereby corrected as shown below:

<u>Column 5,</u>  
Lines 58-64, delete "Using a material for forming the heaters which is different from the material used to form the layers allows the resistance through the heaters to be easily adjusted by varying various parameters including, for example, the dimensions and amount of heat produced by the heaters may be adjusted for various applications. the material of the heaters. In this manner, the resistance of the heaters and the"

and insert therefore -- Using a material for forming the heaters which is different from the material used to form the layers allows the resistance through the heaters to be easily adjusted by varying various parameters including, for example, the dimensions and the material of the heaters. In this manner, the resistance of the heaters and the amount of heat produced by the heaters may be adjusted for various applications. --.

Signed and Sealed this

Fifteenth Day of April, 2003

JAMES E. ROGAN  
*Director of the United States Patent and Trademark Office*